United States Patent
Yuds et al.

(10) Patent No.: US 10,596,311 B2
(45) Date of Patent: Mar. 24, 2020

(54) FIBER-OPTIC CLOT DETECTOR WITH AN ULTRASONIC CLOT NEUTRALIZER

(71) Applicant: Fresenius Medical Care Holdings, Inc., Waltham, MA (US)

(72) Inventors: David Yuds, Hudson, NH (US); Sameera Anirudh Peesapati, Pittsburg, CA (US); Martin Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 16/405,558

(22) Filed: May 7, 2019

(65) Prior Publication Data

US 2019/0358388 A1 Nov. 28, 2019

Related U.S. Application Data

(60) Provisional application No. 62/676,570, filed on May 25, 2018.

(51) Int. Cl.
*A61M 1/36* (2006.01)
*A61M 1/14* (2006.01)

(52) U.S. Cl.
CPC ............ *A61M 1/3609* (2014.02); *A61M 1/14* (2013.01); *A61M 1/367* (2013.01); *A61M 1/3672* (2013.01); *A61M 2202/0478* (2013.01); *A61M 2205/18* (2013.01); *A61M 2205/331* (2013.01)

(58) Field of Classification Search
CPC ...... A61M 1/3609; A61M 1/14; A61M 1/367; A61M 1/3672; A61M 2202/0478; A61M 2205/18; A61M 2205/331
See application file for complete search history.

(56) References Cited

U.S. PATENT DOCUMENTS

| | | | |
|---|---|---|---|
| 4,976,157 | A | 12/1990 | Berthold et al. |
| 2009/0091741 | A1 | 4/2009 | Dogariu |
| 2013/0155387 | A1 | 6/2013 | Wiktor |
| 2016/0258968 | A1 | 9/2016 | Jain et al. |
| 2017/0000940 | A1 | 1/2017 | Schultz et al. |

OTHER PUBLICATIONS

International Patent Application No. PCT/US2019/032662, Search Report (dated Jul. 22, 2019).
Garcia et al., "Vibration Detection Using Optical Fiber Sensors," *J. of Sensors*, vol. 2010 (2010).
Guzman-Sepulveda et al., "Real-Time Intraoperative Monitoring of Blood Coagulability Via Coherence-Gated Light Scattering," *Nature Biomedical Engineering* (Feb. 10, 2017).
Kingery, Ken, "Sound Waves Could Provide 'Liquid Biopsies'," Duke University, *Pratt Intranet* (Jul. 3, 2018).

(Continued)

*Primary Examiner* — Leslie R Deak
(74) *Attorney, Agent, or Firm* — Leydig, Voit & Mayer, Ltd.

(57) ABSTRACT

A method and system for detecting and neutralizing blood clots during dialysis (e.g., hemodialysis) is provided. A fiber-optic sensor is provided in a hemodialysis machine to detect vibration of blood cells, and the hemodialysis machine can be configured to prevent blood clotting by sounding an alarm, agitating the blood cells, infusing saline, raising temperature and/or infusing heparin.

20 Claims, 10 Drawing Sheets

(56) References Cited

OTHER PUBLICATIONS

Nguyen et al., "Flow Rate Measurement in Microfluidics Using Optical Sensors," *1st International Conference on Sensing Technology*, Palmerston North, New Zealand (Nov. 21-23, 2005).

Schlueb, Mark, "Light Beam Replaces Blood Test During Heart Surgery," *University of Central Florida News/UCF Today*, (Feb. 20, 2017).

Shung, K. Kirk, "High Frequency Ultrasonic Imaging," *J. Med. Ultrasound.*, 17(1), 25-30 (2009).

Wongsaroj et al., "Extended Short-Time Fourier Transform for Ultrasonic Velocity Profiler on Two-Phase Bubbly Flow Using a Single Resonant Frequency" *Appl. Sci.* 9(1) (2019).

FIBER-OPTIC CLOT DETECTOR WITH AN ULTRASONIC CLOT NEUTRALIZER

CROSS-REFERENCE TO RELATED APPLICATIONS

This patent application claims the benefit of U.S. Provisional Patent Application No. 62/676,570, filed May 25, 2018, which is incorporated by reference herein in its entirety.

BACKGROUND

Patients with kidney failure or partial kidney failure typically undergo hemodialysis treatment, often at a hemodialysis treatment center or clinic. When healthy, kidneys maintain the body's internal equilibrium of water and minerals (e.g., sodium, potassium, chloride, calcium, phosphorous, magnesium, and sulfate). The kidneys also function as part of the endocrine system to produce the hormone erythropoietin as well as other hormones. Hemodialysis is an imperfect treatment to replace kidney function, in part, because it does not correct the endocrine functions of the kidney.

In hemodialysis, blood is taken from a patient through an intake needle (or catheter) which draws blood from an artery located in a specific accepted access location (arm, thigh, subclavian, etc.). The drawn blood is pumped through extracorporeal tubing via a peristaltic pump, and then through a special filter termed a "dialyzer." The dialyzer is intended to remove unwanted toxins such as blood urea, nitrogen, potassium, and excess water from the blood. As the blood passes through the dialyzer, it travels in straw-like tubes which serve as semi-permeable membrane passageways for the uncleaned blood. Fresh dialysate liquid, which is a solution of chemicals and water, flows through the dialyzer in the direction opposite the blood flow. As the dialysate flows through the dialyzer, it surrounds the straw-like membranes in the dialyzer. These membranes feature small holes which are large enough to pass liquid and liquid based impurities—but are not large enough to pass red blood cells. The fresh dialysate collects excess impurities passing through the straw-like tubes by diffusion, and also collects excess water through an ultrafiltration process due to a pressure drop across the membranes. During this process, the red cell volume is preserved inside the straw-like tubes and recirculated back into the body. The used dialysate exits the dialyzer with the excess fluids and toxins via an output tube, thus cleansing the blood and red cell volume flowing through the dialyzer. The dialyzed blood then flows out of the dialyzer via tubing and a needle (or catheter) back into the patient. Sometimes, a heparin drip or pump is provided along the extracorporeal blood flow loop in order to prevent red cell clotting during the hemodialysis process. Several liters of excess fluid can be removed during a typical multi-hour treatment session. In the U.S., a chronic patient will normally undergo hemodialysis treatment in a dialysis center three times per week, either on Monday-Wednesday-Friday schedule or a Tuesday-Thursday-Saturday schedule. These in-center treatments are typically completed over 3 to 4 hours with blood flow rates typically above 300 ml/minute. In other countries, the flow rates and time for treatment are lower and longer, respectively.

Hemodialysis has an acute impact on the fluid balance of the body due in part to the rapid change in circulating blood volume. When the dialysis fluid removal rate is more rapid than the plasma refilling rate of the stored plasma held by the internal tissue of the body, intravascular blood volume decreases. The resulting imbalance has been linked to complications similar to conventional blood loss such as hypotension, loss of consciousness, headaches, vomiting, dizziness and cramps experienced by the patient, both during and after dialysis treatments. Continuous quantitative measurement of parameters relating to the processing of the blood volume (in real-time) during hemodialysis can reduce the chance of dialysis-induced hypotension, and otherwise optimize dialysis therapy regimens by controlling fluid balance and aiding in achieving the target dry weight for the patient.

During a hemodialysis treatment, a patient's blood is circulated outside of the patient's body in order to filter out toxins via a dialyzer. Air in the bloodlines, whether remaining there from insufficient removal during priming or produced at the blood-air interface found in drip chambers causes clotting over time. Clotting reduces treatment efficacy and may require blood to be discarded if blood flow is stopped. As a result, heparin (a naturally occurring anticoagulant) may be steadily infused into the bloodstream via a pump in order to reduce the likelihood of clots.

SUMMARY

Embodiments of the disclosure provide a method for monitoring blood clotting. The method includes: circulating, by a dialysis system, blood through an extracorporeal circuit, wherein the blood flows from a patient to an input tubing of the extracorporeal circuit then to a dialyzer of the dialysis system and then back to the patient via an output tubing of the extracorporeal circuit; measuring, by a fiber-optic sensor of the dialysis system, blood vibration frequency of the blood flowing through the extracorporeal circuit; determining, by the dialysis system, whether the blood vibration frequency is below a threshold; and performing, by the dialysis system, a remedial process to address blood clotting in response to the blood vibration frequency being below the threshold.

Embodiments of the disclosure provide a dialysis system for monitoring blood clotting. The dialysis system includes: a pump for pumping blood from a patient through an extracorporeal circuit; a dialyzer connected to the extracorporeal circuit; a fiber-optic sensor interfacing with the extracorporeal circuit, wherein the fiber-optic sensor is configured to measure blood vibration frequency at a location along the extracorporeal circuit; and a controller configured to: determine whether the blood vibration frequency is below a threshold, and perform a remedial process to address blood clotting in response to the blood vibration frequency being below the threshold.

Embodiments of the disclosure provide a non-transitory computer readable medium having computer executable instructions stored thereon for monitoring blood clotting in a dialysis system. The computer executable instructions, when executed, facilitate: circulating blood through an extracorporeal circuit; measuring blood vibration frequency of the blood flowing through the extracorporeal circuit; determining whether the blood vibration frequency is below a threshold; and performing a remedial process to address blood clotting in response to the blood vibration frequency being below the threshold.

DETAILED DESCRIPTION

Heparin is a costly drug and over-use can be hazardous to a patient's health, preventing clotting when disconnecting the patient at the end of his/her treatment. Furthermore, a problem in dialysis is estimating how much heparin is to be prescribed for any particular patient, with some of it either going to waste or treatment delays resulting from insufficient heparin. Additionally, some patients are allergic to heparin and alternatives like saline is used to break up blood clots through direct and costly monitoring by a clinician.

Some embodiments of the disclosure monitor clotting in real-time and target those clots with precise heparin infusions. The monitoring is accomplished by use of a fiber-optic sensor and targeting the clots may be accomplished by interpreting software linked to the heparin pump. The use of the fiber-optic sensor and the software-controlled heparin pump may reduce costs of a hemodialysis treatment and prevent over-heparinization of patients, thereby improving health outcomes.

Some embodiments of the disclosure monitor clotting in real-time and target those clots with ultrasonic vibrations. When a fiber-optic sensor detects blood cells vibrating more slowly, an ultrasonic head may be vibrated to blast the clotting mass before it reaches a critical size. The ultrasonic head produces sound waves at a frequency/wavelength to cause blood cells to vibrate more vigorously again, effectively breaking up the clot because the clot can no longer hold itself together.

Figure 1:
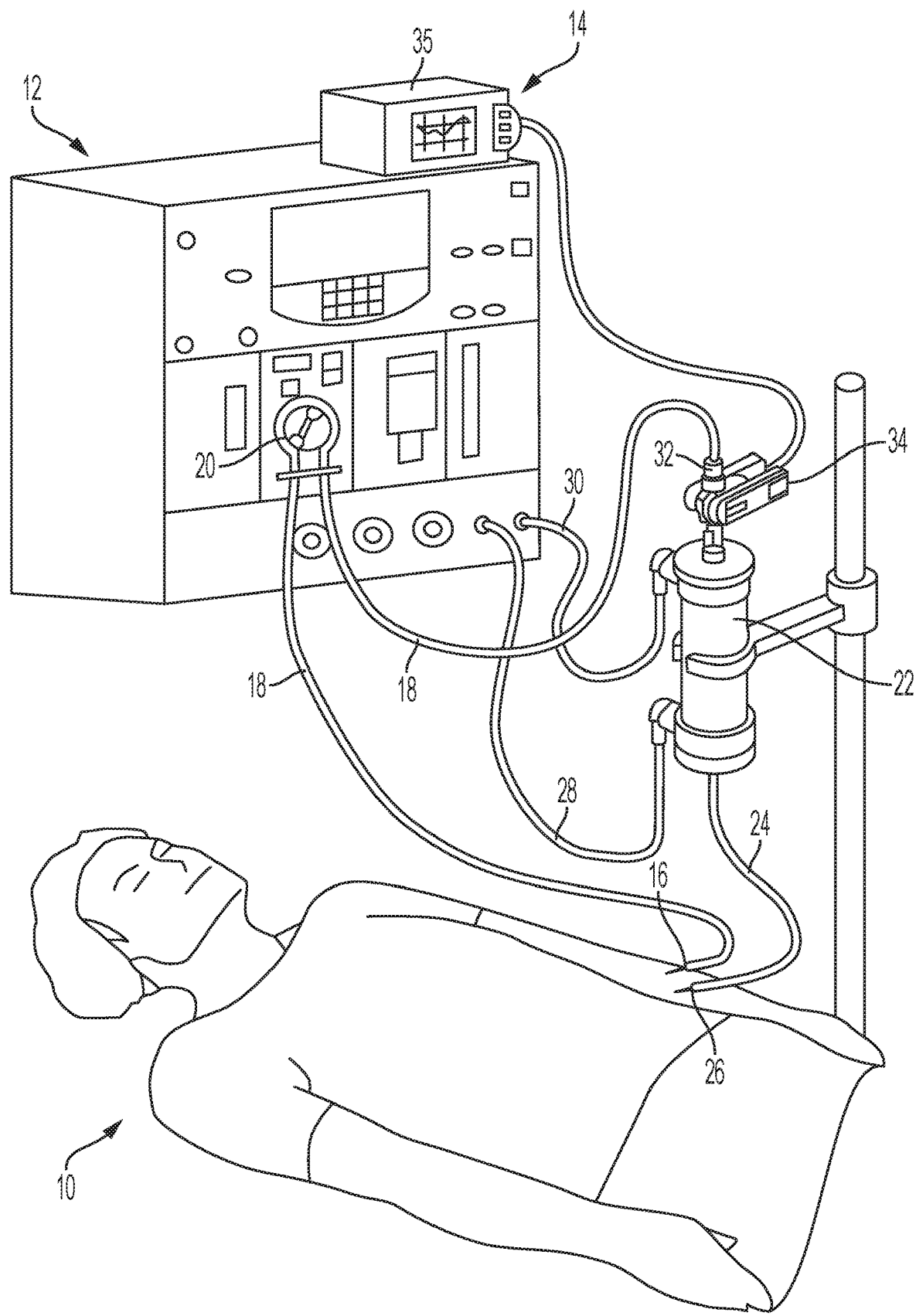
FIG. 1 is a perspective view of a typical patient undergoing hemodialysis treatment with a non-invasive, optical blood monitor monitoring the patient's blood in real-time as it passes through extracorporeal tubing in the hemodialysis system.

FIG. 1 is a perspective view of an exemplary patient undergoing hemodialysis treatment with a non-invasive, optical blood monitor monitoring the patient's blood in real-time as it passes through extracorporeal tubing in the hemodialysis system. The environment illustrated in FIG. 1 is usable with exemplary embodiments of the present disclosure. Further, it will be appreciated that the environment shown in FIG. 1 is merely exemplary, and that the principles discussed herein with respect to exemplary embodiments of the present disclosure may be implemented in other environments as well.

FIG. 1 illustrates a patient 10 undergoing hemodialysis treatment using a conventional hemodialysis system 12, as well as a non-invasive, optical blood monitor 14. A typical hemodialysis clinic will have several hemodialysis systems 12 for treating patients on a Monday-Wednesday-Friday schedule or a Tuesday-Thursday-Saturday schedule. While the invention is not limited to the number of hemodialysis systems located at a clinic, or the specific type of hemodialysis system, the general operation of the hemodialysis system 12 is helpful for understanding the environment in which the invention is intended to operate.

An input needle or catheter 16 is inserted into an access site of the patient 10, such as in the arm, and is connected to extracorporeal tubing 18 that leads to a peristaltic pump 20 and then to a dialyzer or blood filter 22. The dialyzer 22 removes toxins and excess fluid from the patient's blood. The dialyzed red cell blood volume is returned from the dialyzer 22 through extracorporeal tubing 24 and return needle or catheter 26. In some parts of the world (primarily the United States), the extracorporeal blood flow may additionally receive a heparin drip to prevent clotting. The excess fluids and toxins are removed by clean dialysate liquid, which is supplied to the dialyzer 22 via tube 28 and removed for disposal via tube 30. A typical hemodialysis treatment session takes about 3 to 5 hours in the United States.

In the exemplary environment depicted in FIG. 1, the optical blood monitor 14 includes a blood chamber 32, an optical blood sensor assembly 34, and a controller 35. The blood chamber 32 may be located in line with the extracorporeal tubing 18 upstream of the dialyzer 22. Blood from the peristaltic pump 20 flows through the tubing 18 into the blood chamber 32. In some embodiments, the blood chamber 32 is not provided, and the optical blood sensor assembly 34 is directly coupled to the extracorporeal tubing 18. The optical blood sensor assembly 34 may include a fiber-optic sensor for measuring a vibration rate of individual blood cells.

Embodiments of the disclosure incorporate a fiber-optic sensor into a hemodialysis machine, for example, the hemodialysis system 12, and the fiber-optic sensor can interpret how rapidly red blood cells are clotting. Using analysis in heterodyne amplification, complex media, such as blood, can be analyzed to determine a vibration rate of individual cells in the blood stream. Clotting may be indicated by vibration of the blood cells, that is, clotting causes cells to vibrate more slowly.

Figure 2:
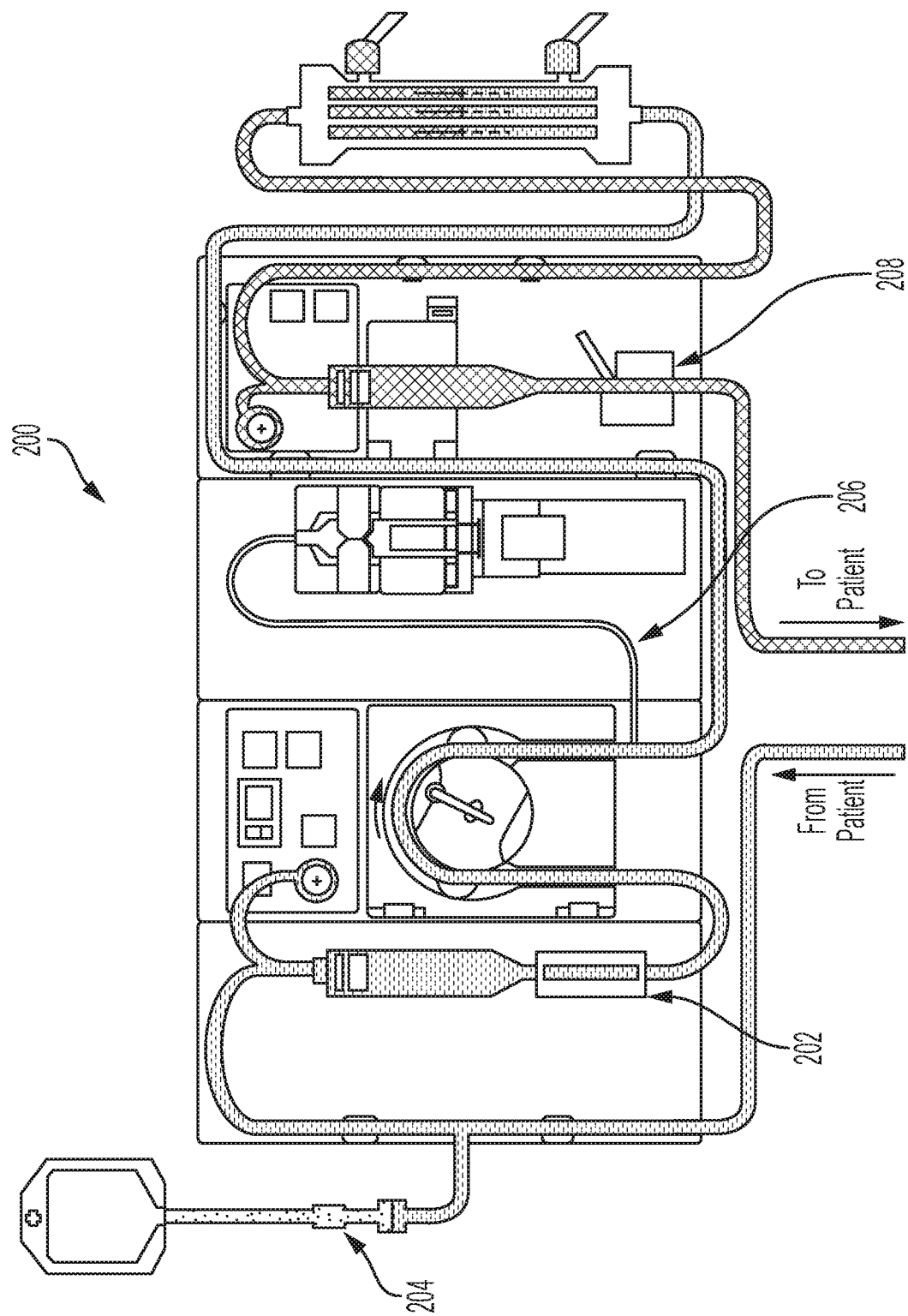
FIG. 2 illustrates an exemplary system for performing hemodialysis showing a first location for a fiber-optic sensor according to some embodiments of the disclosure.

FIG. 2 illustrates an exemplary system configuration 200 for hemodialysis treatment according to some embodiments of the disclosure. The system configuration 200 may include an optical sensor assembly 202 with a fiber-optic sensor placed after a saline tubing input 204 and before a heparin tubing input 206. An example of a fiber-optic sensor that can be used in the optical sensor assembly 202 includes the Baumer FSE 100F6Y01 sensor. The system configuration 200 may also include an air bubble detector 208. The optical sensor assembly 202 is shown to be installed right below the arterial drip chamber. During hemodialysis, the optical sensor assembly 202 may monitor vibration of blood coming from a patient to determine whether heparin should be infused using the heparin tubing input 206.

Figure 3:
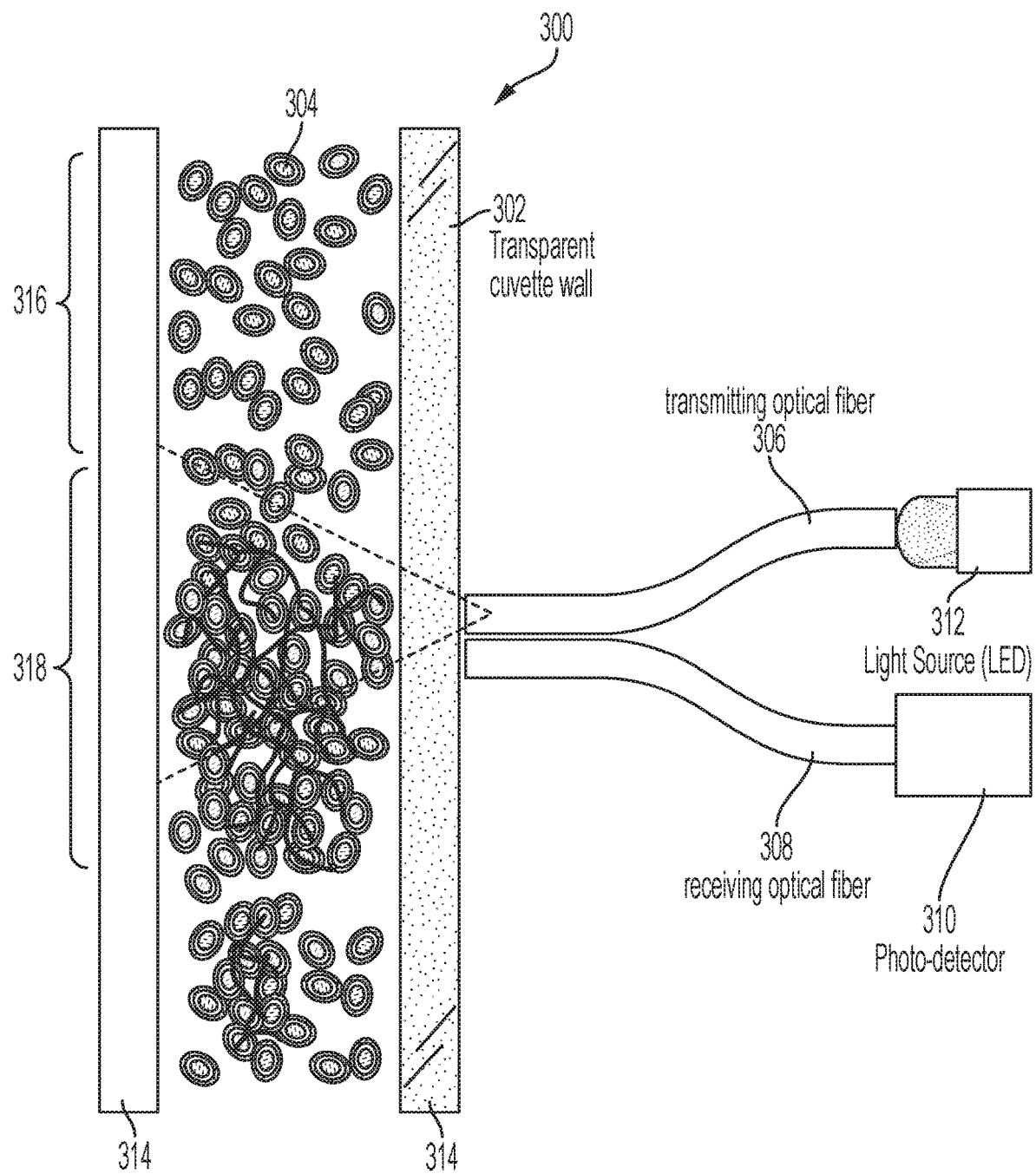
FIG. 3 illustrates an example fiber-optic sensor according to some embodiments of the disclosure.

FIG. 3 illustrates an example optical sensor assembly 300 including a cuvette 314 with a transparent cuvette wall 302, a transmitting optical fiber 306, a receiving optical fiber 308, a light source 312, and a photodetector 310. The cuvette 314 can be a plastic tubing or glass chamber with the transparent cuvette wall 302. The transmitting optical fiber 306 transmits light from the light source 312 to the cuvette 314 for illuminating blood flowing through the cuvette 314. In an embodiment, the light source 312 provides light with wavelength ranging from 635 nm to 700 nm. Blood cells 304 interact with the transmitted light and reflect some of the light. The reflected light is received by the receiving optical fiber 308 and guided to the photodetector 310.

The light received at the photodetector is dependent on the spacing between blood cells 304 which indicates a vibrating of the blood cells 304. Clotting causes the blood cells 304 to vibrate more slowly and will therefore have a higher amplitude of reflected light compared to blood cells 304 that are not clotting. For example, section 316 when illuminated by the light source 312 will have a lower amplitude of reflected light compared to section 318. In an embodiment, the light source 312 is a light emitting diode (LED), and the LED, photodetector 310, receiving optical fiber 308 and transmitting optical fiber 306 comprise a fiber-optic sensor of the fiber-optic sensor assembly 300.

Figure 4:
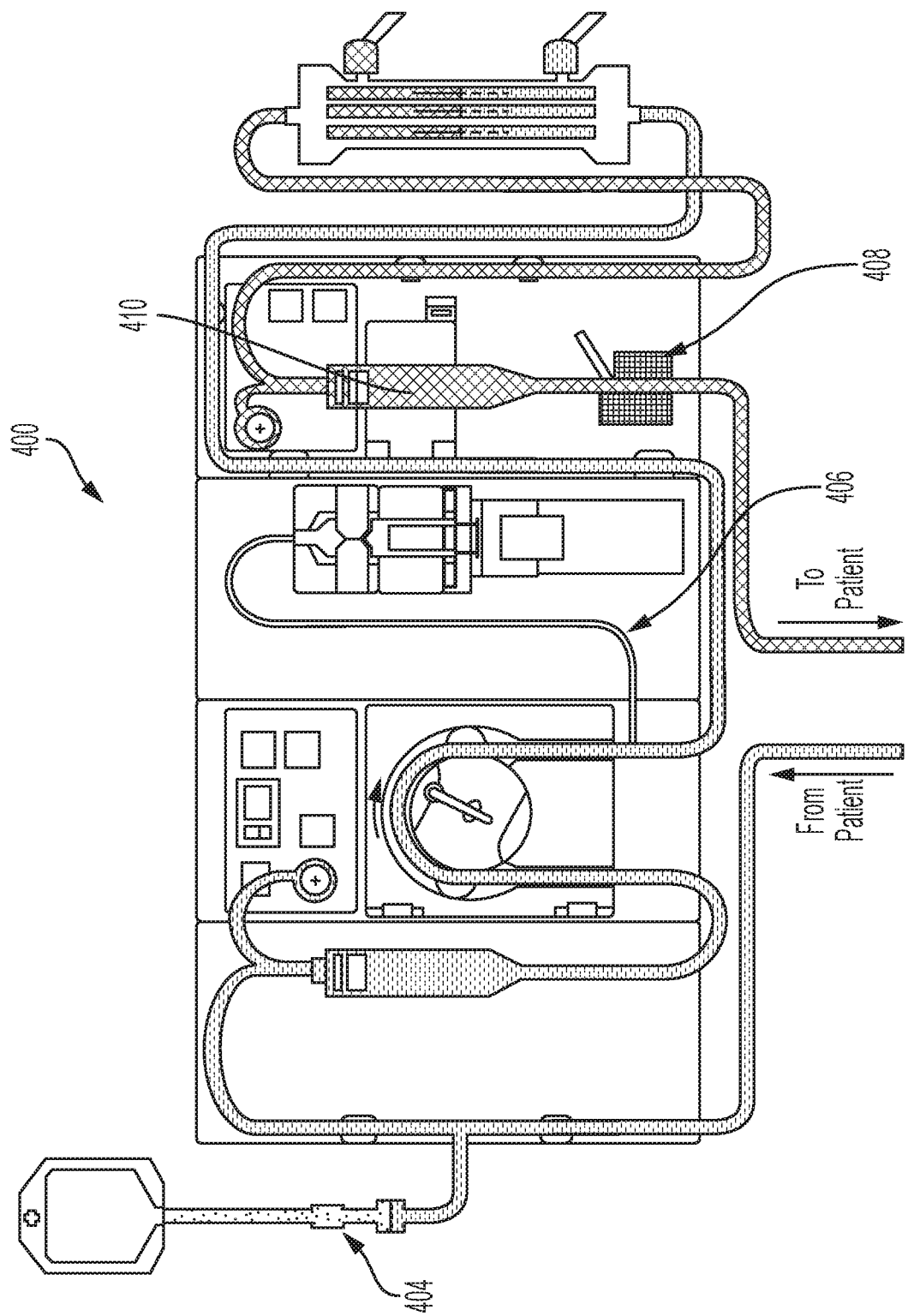
FIG. 4 illustrates an exemplary system for performing hemodialysis showing a second location for a fiber-optic sensor according to some embodiments of the disclosure.

FIG. 4 illustrates an exemplary system configuration 400 for hemodialysis treatment according to some embodiments of the disclosure. The system configuration 400 includes an optical sensor assembly 408 with a fiber-optic sensor placed after a heparin tubing input 406. During hemodialysis, the optical sensor assembly 408 may monitor vibration of blood cells going into the patient to determine whether heparin should be infused using the heparin tubing input 406. In FIG. 4, the optical sensor assembly 408 is placed at a location of an existing bubble-detector in the venous clamp below a venous drip chamber 410. An advantage of this location is that no new connection point is added to a clinician's workflow, and the optical sensor assembly 408 can be used to detect both clots and air bubbles, simplifying and reducing the cost of incorporating a clot monitoring feature in a dialysis machine.

Figure 5:
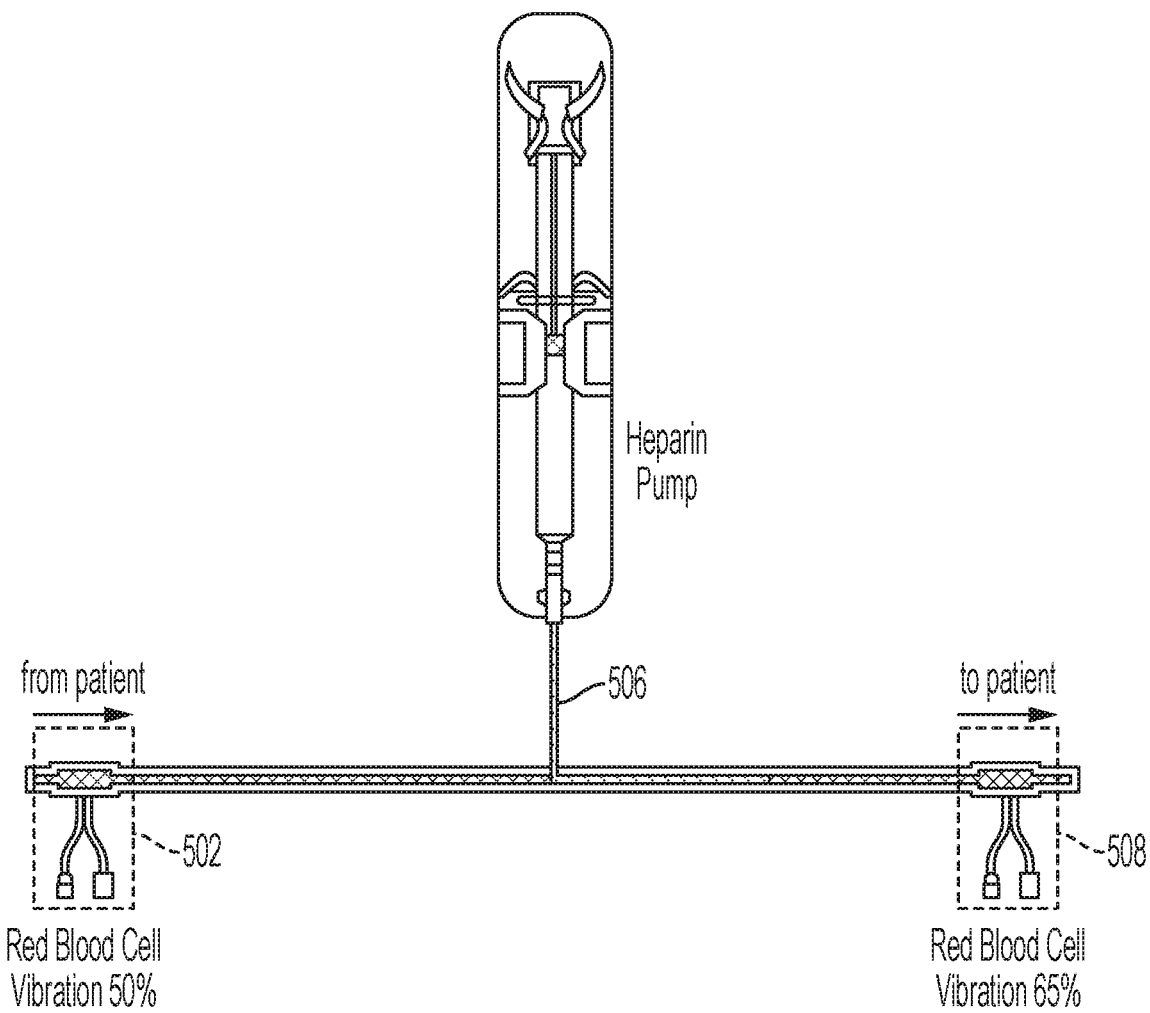
FIG. 5 illustrates using two fiber-optic sensors for measuring heparin efficacy according to an embodiment of the disclosure.

FIG. 2 and FIG. 4 show two placements of optical sensor assemblies, one before heparin tubing input 206 and one after heparin tubing input 406. Other configurations that have two fiber-optic sensors may be used where blood vibrations before heparin infusion is measured and blood vibrations after heparin infusion is also measured to determine efficacy of the heparin infusion. FIG. 5 includes an example of such a configuration which utilizes two optical assemblies (optical assembly 502 and optical assembly 508) to monitor blood vibrations both before and after heparin. In an example, as illustrated in FIG. 5, before heparin infusion, the optical assembly 502 can measure red blood cell vibration of 50%, and after heparin infusion, the optical assembly 508 can measure red blood cell vibration of 65%. The 15% difference indicates efficacy of heparin infusion via the heparin tubing input 506. Heparin infusion is discussed as an example, but a similar process can be used to determine saline infusion efficacy.

In some embodiments, software running on the hemodialysis system 12 may interpret the blood cell vibration and directly control a heparin pump to infuse heparin. The control of the heparin pump using the software may reduce heparin usage, which facilitates smaller amounts of heparin to be pre-loaded into the hemodialysis system 12. Furthermore, if the hemodialysis system 12 anticipates higher likelihoods of clotting or more frequent clotting based on vibration monitoring, the hemodialysis system 12 can notify a clinician if the remaining heparin is too low to continue. The notification may take a form of generating an alarm.

In some embodiments, the hemodialysis system 12 monitors the feedback from a fiber-optic sensor and creates models of how the vibration rate of the blood cells varies through subsequent loops in the extracorporeal blood circuit. For example, for a given blood pump rate and a patient's total blood volume, the hemodialysis system 12 estimates a recirculation time, i.e., time that it takes before the same blood is processed again by the hemodialysis system 12. The hemodialysis makes an initial red blood cell vibration measurement $D_0$ at time $t_0$ using an optical sensor assembly according to an embodiment of the disclosure. After the recirculation time, the hemodialysis system 12 makes another measurement $D_1$ at time $t_1$. The separation of times $t_1$ and $t_0$ is the recirculation time, and subsequent measurements $D_n$ are made at intervals of the recirculation time.

After a number of measurements, the hemodialysis machine 12 determines the vibration profile of the patient based on his hematocrit, blood flow rate, and temperature. Each measurement $D_n$ is cross-checked against $D_0$ and $D_1$, yielding efficacy in the form of a rising slope showing increased red blood cell vibration over time. In an embodiment, while creating the models on how the vibration rate of the red blood cells varies through subsequent loops, an ultrasonic sensor operating at a very high frequency (>65 MHz) can be used to measure white blood cell count. That way, the models or profiles created during a dialysis session can be adjusted as a function of white blood cell count as white blood cells fluctuate from one dialysis treatment session to another.

In an embodiment, the hemodialysis system 12 may make recommendations for the clinician based on blood vibration measurements during dialysis. For example, if the hemodialysis system 12 determines that blood vibration measurements are low, the hemodialysis system 12 can recommend a clinician infuse a bolus of 200 ml of normal saline (NS) or 1 ml of heparin into the extracorporeal circuit. In an embodiment, instead of alerting the clinician, the clinician may set the hemodialysis system 12 to automatically infuse an appropriate heparin dose when the hemodialysis system 12 determine that blood vibration measurements are low. In an embodiment, the hemodialysis system 12 provides a visual and/or audible alert to the clinician with the recommendation. The hemodialysis system 12 can include a speaker for providing audio alerts. The hemodialysis system 12 can include multiple displays, e.g., display on the optical blood monitor 14, for providing visual alerts.

In an embodiment, the hemodialysis system 12 automatically periodically adjusts the temperature of the dialysate, for example, in order to make the blood cells more energetic, further reducing heparin usage. For example, when blood vibration measurements are low, the hemodialysis system 12 increases dialysate temperature in steps of 0.25 degrees Celsius to a maximum of 37.5 degrees Celsius before alerting the clinician with a visual and/or audible alert.

In an embodiment, the hemodialysis system 12 correlates with feedback from a combined sensor, like the Crit-Line hematocrit sensor, to prompt the clinician to infuse saline when dry weight is approached before the end of the dialysis treatment time, rather than use more heparin. For example, a goal of dialysis is to get the patient to dry weight within a set dialysis treatment time, so during the last half hour of treatment, the hemodialysis system 12 infuses only saline or alerts a clinician to infuse only saline when needed. That way, during the last half hour of treatment, heparin is not used at all. The hemodialysis system 12 can use an elapsed treatment time or the combined sensor's indication of change in blood volume, since the start of treatment, to determine when to use only saline.

Figure 6:
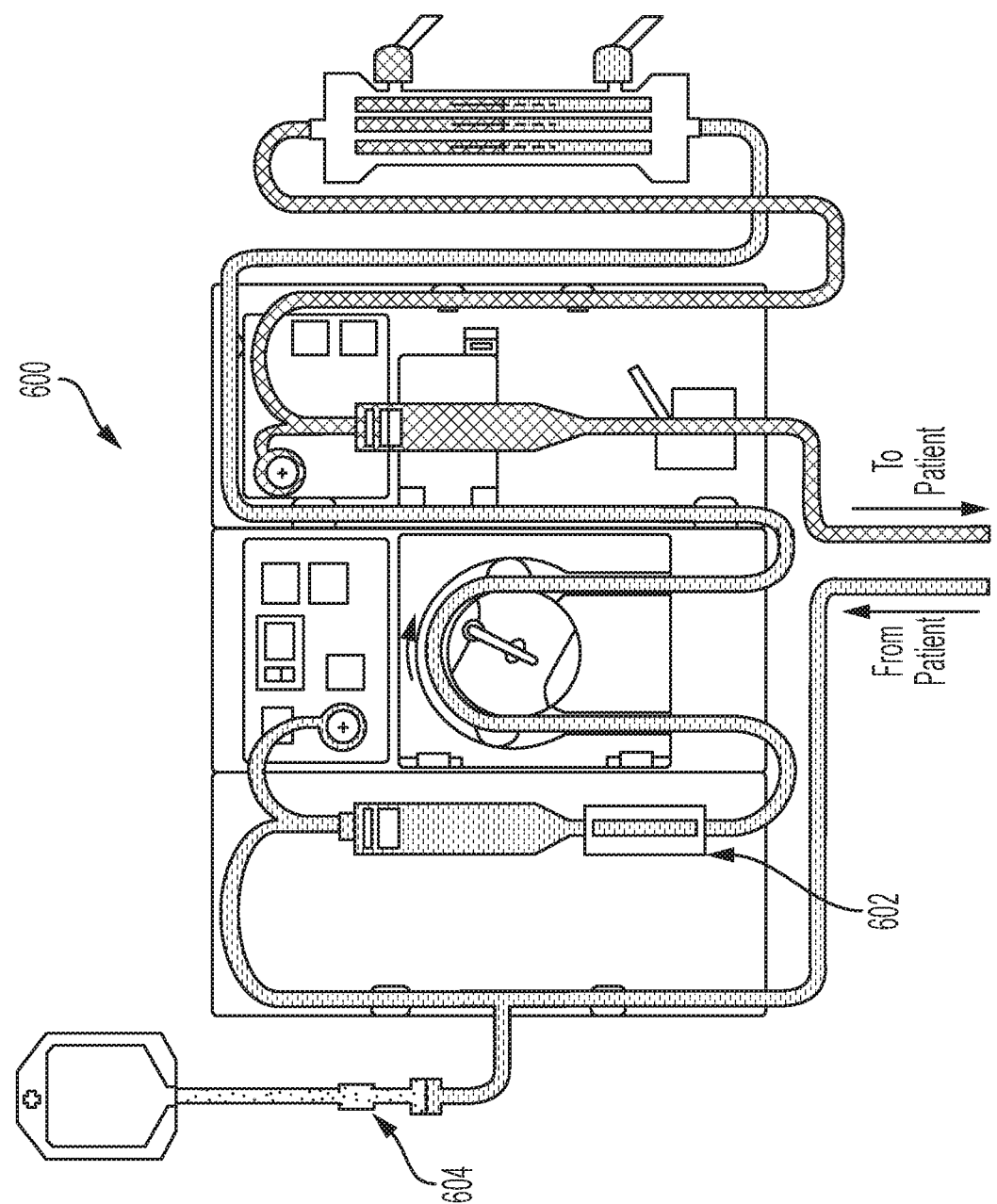
FIG. 6 illustrates an exemplary system for performing hemodialysis showing a first location for a fiber-optic sensor and clot neutralizer device according to some embodiments of the disclosure.

FIG. 6 illustrates an exemplary system configuration 600 for hemodialysis treatment according to some embodiments of the disclosure. The system configuration 600 may include an optical sensor assembly 602 with a fiber-optic sensor and an ultrasonic or piezoelectric head placed downstream, after a saline tubing input 604. Ultrasonic heads that can be used include high frequency transducers designed to produce frequencies of at least 50 MHz, e.g., NDT Instrument U841102 transducer. In some embodiments, laser vibration meters, e.g., PolyTec CLV-2534 Compact Laser Vibrometer, can be used as fiber-optic detectors. When the fiber-optic sensor detects blood cells vibrating more slowly, the hemodialysis machine may activate the ultrasonic head to blast clotting masses before they reach a critical size. The ultrasonic head produces sound waves at a wavelength which causes blood cells to vibrate more vigorously again, effectively breaking up the clot because it can no longer hold itself together. For example, the ultrasonic head can produce sound waves at 65 MHz to break up clots. The system configuration 600 may greatly reduce treatment costs by eliminating a need for heparin or a heparin pump on the hemodialysis machine 12.

Although an ultrasonic head is provided in some embodiments for breaking up clots or blasticing clotting masses before they reach a critical size, other methods of agitating blood can be used. For example, a vibration motor can be placed against tubing, and the hemodialysis machine 12 can turn on the vibration motor to agitate the tubing in order to break up clots detected via the fiber-optic sensor.

In an embodiment, the ultrasonic head can be used to locally detect clots or masses of red blood cells between 20 μm and 100 μm at a lower frequency, e.g., at 50 MHz, and then can be used to break up the clots at a slightly higher frequency, e.g., at 65 MHz.

Figure 7:
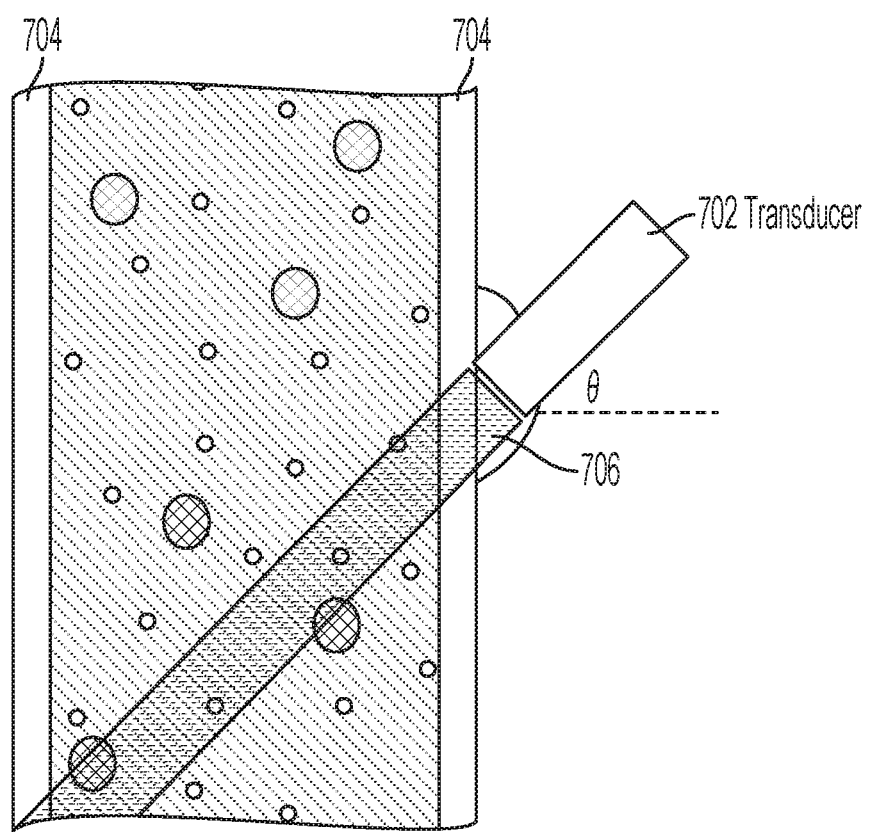
FIG. 7 illustrates placement of an ultrasonic transducer for blasting blood clots according to an embodiment of the disclosure.

FIG. 7 illustrates an ultrasonic head configuration according to an embodiment of the disclosure. The ultrasonic head 702 is placed at an angle to the cuvette 704. The ultrasonic head 702 produces ultrasonic waves 706 for breaking up clots in blood flowing through the cuvette 704.

In some embodiments, software in the hemodialysis system 12 may be used to interpret blood cell vibration and directly control the ultrasonic head. The hemodialysis system 12 monitors the feedback from the fiber-optic sensor and creates models of how the vibration rate of the blood cells varies through subsequent loops in the extracorporeal blood circuit according to embodiments of the disclosure. The hemodialysis system 12 may then make recommendations for the clinician. For example, should clotting become too prevalent due to a system leak, the hemodialysis system 12 may issue an alert in the form of a pop-up or a status box message to the clinician to provide an emergency manual bolus of heparin. In an embodiment, if vibration of blood cells falls below an expected threshold, then the hemodialysis system 12 determines that clotting is detected and automatically infuses a volume of saline into the extracorporeal circuit. The hemodialysis system 12 adds the added saline volume to the dialysis treatment's ultrafiltration goal.

Figure 8:
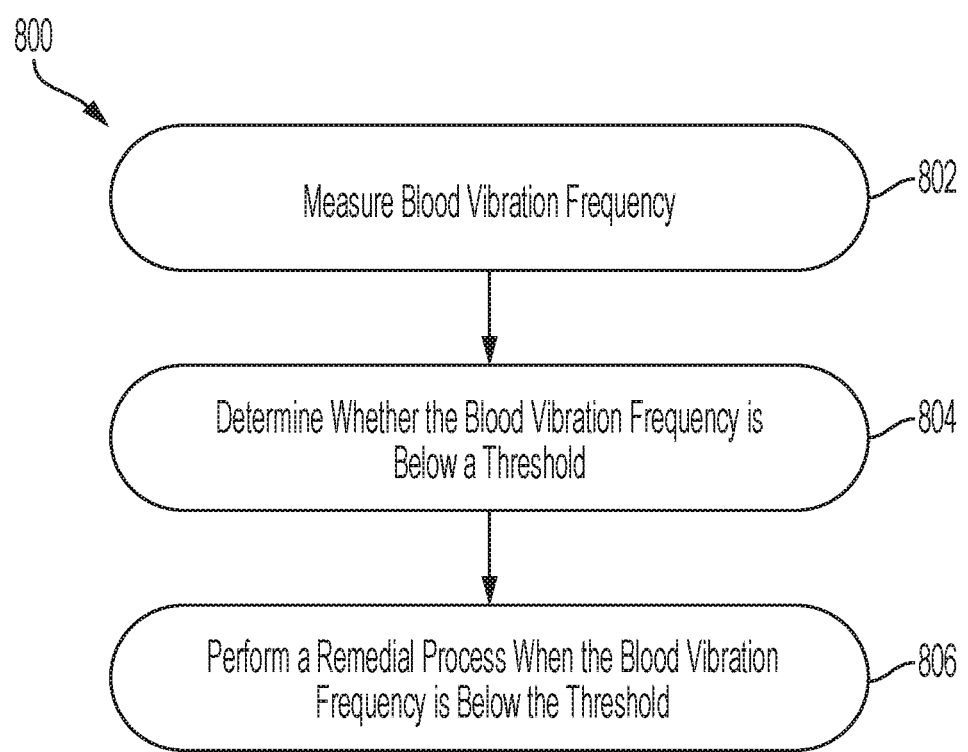
FIG. 8 is a flow diagram illustrating a process for clot neutralization with a fiber-optic sensor according to some embodiments of the disclosure.

FIG. 8 is a flow diagram illustrating a process for clot neutralization with a fiber-optic sensor in a hemodialysis machine 12 according to some embodiments of the disclosure. At step 802, the fiber-optic sensor measures blood vibration frequency. For example, in FIG. 3, the fiber-optic sensor can include light source 312, photo-detector 310, receiving optical fiber 308, and transmitting optical fiber 306. The light source 312 illuminates fluid flowing through a tubing. The fluid, e.g., blood flowing through tubing of a dialysis circuit, produces a deflection in the tube. The fluid also attenuates light transmitted from the transmitting optical fiber 306 to the receiving optical fiber 308 in a manner proportional to the flowrate of fluid in the tube. The hemodialysis machine 12 determines flowrate based on light received at photodetector 310.

The hemodialysis machine 12 can then determine the blood vibration frequency by calculating potential energy of blood at rest (e.g., blood in a vial) versus the kinetic energy of blood at the measured flowrate. The hemodialysis machine 12 can determine mass of blood based on measured hematocrit using e.g., Crit-Line sensor. From the mass and the flowrate, the hemodialysis system 12 determines kinetic energy using $½ \times mass \times velocity^2$, where velocity is the measured flowrate. The kinetic energy, e.g., in units of Joules, is taken as the blood vibration frequency.

At step 804, the blood vibration frequency is compared against a threshold. The threshold may be different for each patient and can be calibrated on a per-patient basis. The threshold may be affected by a blood pump rate, a performance of access flow, hematocrit, temperature, and percentage of white blood cells. Prior testing and calibration for each patient is used to determine the patient's threshold.

In an embodiment, since blood vibration frequency and temperature are linked, blood temperature can be used as an upper threshold limit. Blood temperature is monitored by the hemodialysis system 12 using temperature sensors, such that it does not exceed 39 degrees Celsius.

At step 806, the hemodialysis machine 12 performs a remedial process, which may include making adjustments to the operation of the hemodialysis machine 12, when the blood vibration frequency is below the threshold of step 804. In one aspect, the hemodialysis machine 12 may control a heparin pump, infusing heparin when the blood vibration frequency is below the threshold as described above with respect to FIG. 4.

In another aspect, the hemodialysis machine 12 may control an ultrasonic head, generating sounds waves to agitate the blood in order to increase the blood vibration frequency. For example, if the blood vibration frequency measured at step 802 is below the threshold at step 804, then clotting is detected. The hemodialysis machine 12 can provide signals to instruct the ultrasonic head to emit a series of brief ultrasonic bursts at an empirically determined frequency. In an embodiment, a brief ultrasonic burst is on the order of milliseconds because blood moving through tubing at up to 500 ml/min during dialysis will have clots pass the ultrasonic head quickly.

A second vibration sensor, e.g., a fiber-optic sensor, placed downstream from the ultrasonic head can be used to verify that the clot is broken up. Since the blood flowrate through the extracorporeal circuit is known, the second vibration sensor can measure clotting at a specific time after emission of the series of brief ultrasonic bursts.

Breaking up clots using the ultrasonic head can follow multiple algorithms determined via testing using a feedback monitoring loop in a lab setting. For example, the ultrasonic head can emit a constant low frequency in the range of 20 Hz that "stirs" red blood cells such that they cannot form clots. In another example, the ultrasonic head can emit a series of brief bursts at 50 MHz to sever long chains of red blood cells.

In another aspect, the hemodialysis machine 12 may sound an alarm when the blood vibration frequency is below the threshold. Multiple types of alarms may be set up, for example, an alarm for a clinician to infuse saline instead of heparin if the conclusion of treatment is approaching. Another alarm may be set up to prompt the clinician for an emergency manual bolus of heparin. Another alarm may be set up to prompt the clinician to increase the temperature of dialysate used during the hemodialysis treatment or to reduce blood pump rate.

Figure 9:
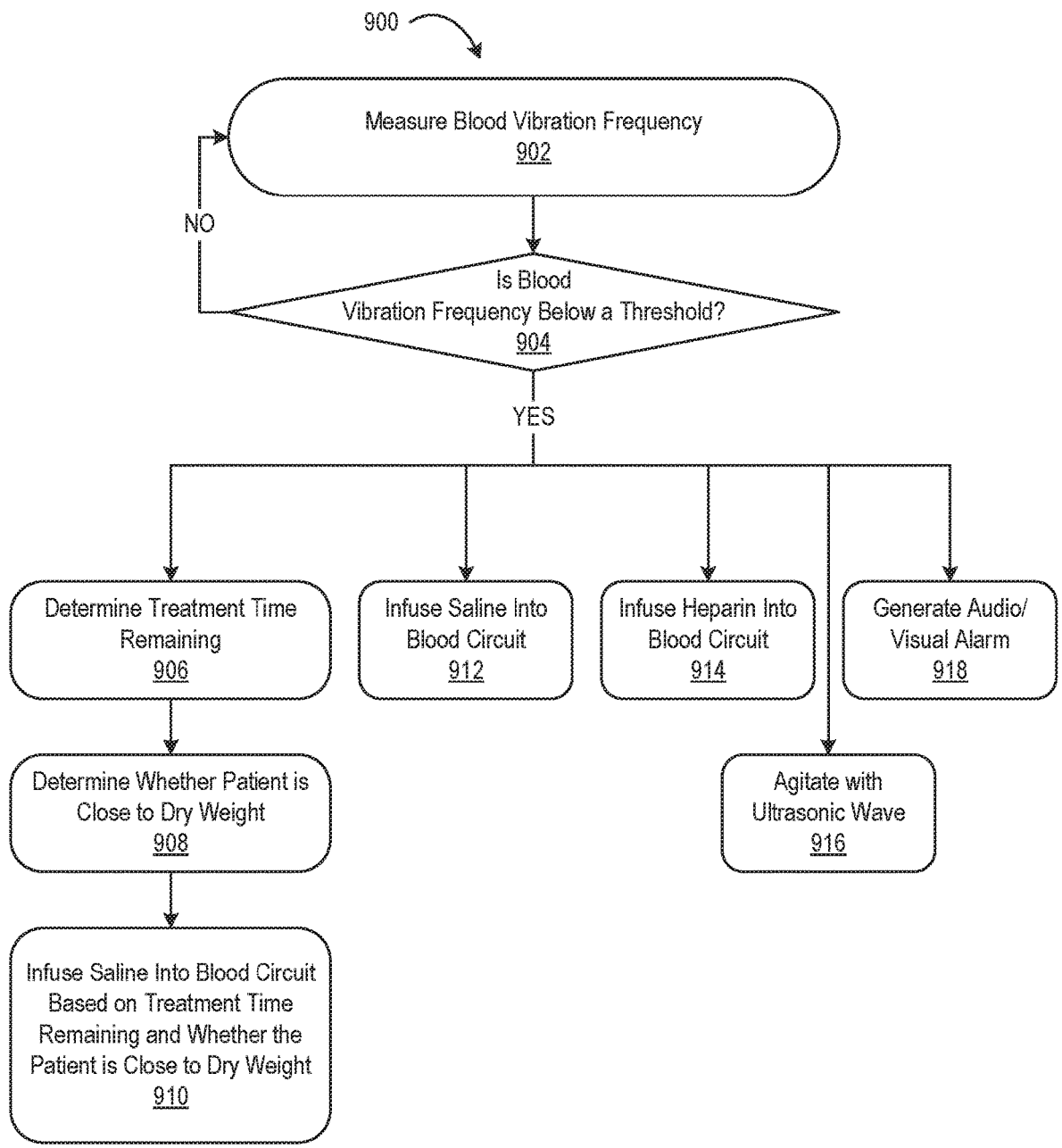
FIG. 9 is a flow diagram illustrating a process for clot neutralization with a fiber-optic sensor according to some embodiments of the disclosure.

FIG. 9 is a flow diagram illustrating a process 900 for clot neutralization with a fiber-optic sensor according to some embodiments of the disclosure. FIG. 9 illustrates examples of step 806 of FIG. 8. At 902, the hemodialysis machine 12 uses the fiber-optic sensor to measure blood vibration frequency. At 904, the hemodialysis machine 12 determines whether the blood vibration frequency is below a threshold. If the blood vibration frequency is above the threshold, the hemodialysis machine 12 continues measuring blood vibration frequency at 902. If the blood vibration frequency is above the threshold, the hemodialysis machine 12 performs a remedial process (e.g., by taking one or more of the five paths depicted in FIG. 9).

In a first path, at 906, the hemodialysis machine 12 determines remaining treatment time. At 908, the hemodialysis machine determines whether the patient is close to dry weight based on the remaining treatment time or based on hematocrit as discussed earlier. At 910, if the remaining treatment time is below a threshold, e.g., 30 minutes, and/or if the dialysis patient is close to dry weight, the hemodialysis machine 12 infuses only saline into the blood circuit. The volume of saline that is added may be a preset amount (e.g., between 10 ml and 500 ml). The preset amount may be selected by an authorized user of the hemodialysis machine (e.g., in a service mode of the machine). The preset amount may also be based on remaining treatment time (e.g., 200 ml with 30 minutes remaining, 150 ml with 20 minutes remaining, 100 ml with 10 minutes remaining, and 50 ml with 5 minutes or less remaining).

In a second path, if the blood vibration frequency is below the threshold at step 904, then at step 912, the hemodialysis machine 12 infuses saline into the blood circuit. The volume of saline that is added may be a preset amount determined in a manner similar as discussed above.

In a third path, if the blood vibration frequency is below the threshold at step 904, then at step 914, the hemodialysis machine 12 infuses heparin into the blood circuit. The volume of heparin that is added may be a preset amount (e.g., between 0.5 ml and 1.5 ml). The preset amount may be selected by an authorized user of the hemodialysis machine (e.g., in a service mode of the machine). The preset amount may also be based on remaining treatment time (e.g., 1.5 ml with 3 hours remaining, 1 ml with 2 hours remaining, 0.5 ml with 1 hour remaining, and 0.25 ml with down to 30 minutes remaining, and no heparin infused beyond the 30 minutes remaining mark). Additionally, the hemodialysis machine 12 may be configured to wait a certain amount of time after infusing an amount of heparin before infusing any additional heparin to ensure that the first infusion has time to take effect (e.g., the machine may include a requirement to wait at least 1 hour between heparin infusions).

In a fourth path, if the blood vibration frequency is below the threshold at step 904, then at step 916, the hemodialysis machine 12 agitates blood within the blood circuit with ultrasonic wave using the ultrasonic head, according to embodiments of the disclosure. The agitation process may include a short burst (e.g., lasting a few microseconds) targeted at a detected clot. The timing of the burst may be based on the location of the ultrasonic head relative to the fiber-optic sensor and the blood flow rate (e.g., the blood pump rate may be 10-600 ml/min). Additionally, the hemodialysis machine 12 may be able to distinguish between detecting the same clot again versus detecting a new clot based on a blood recirculation time (calculated based on the blood pump rate), such that the hemodialysis machine 12 is able to determine whether the agitation process was able to successfully break up a clot.

In a fifth path, if the blood vibration frequency is below the threshold at step 904, then at step 918, the hemodialysis machine 12 generates an audio/visual alarm for the clinician. In some embodiments, step 918 is performed with any one of the other paths. For example, the hemodialysis machine 12 may indicate that a volume of heparin is being added in response to the blood vibration frequency being below a threshold, and may further alert the clinician if clotting is still sensed despite the heparin being added.

Figure 10:
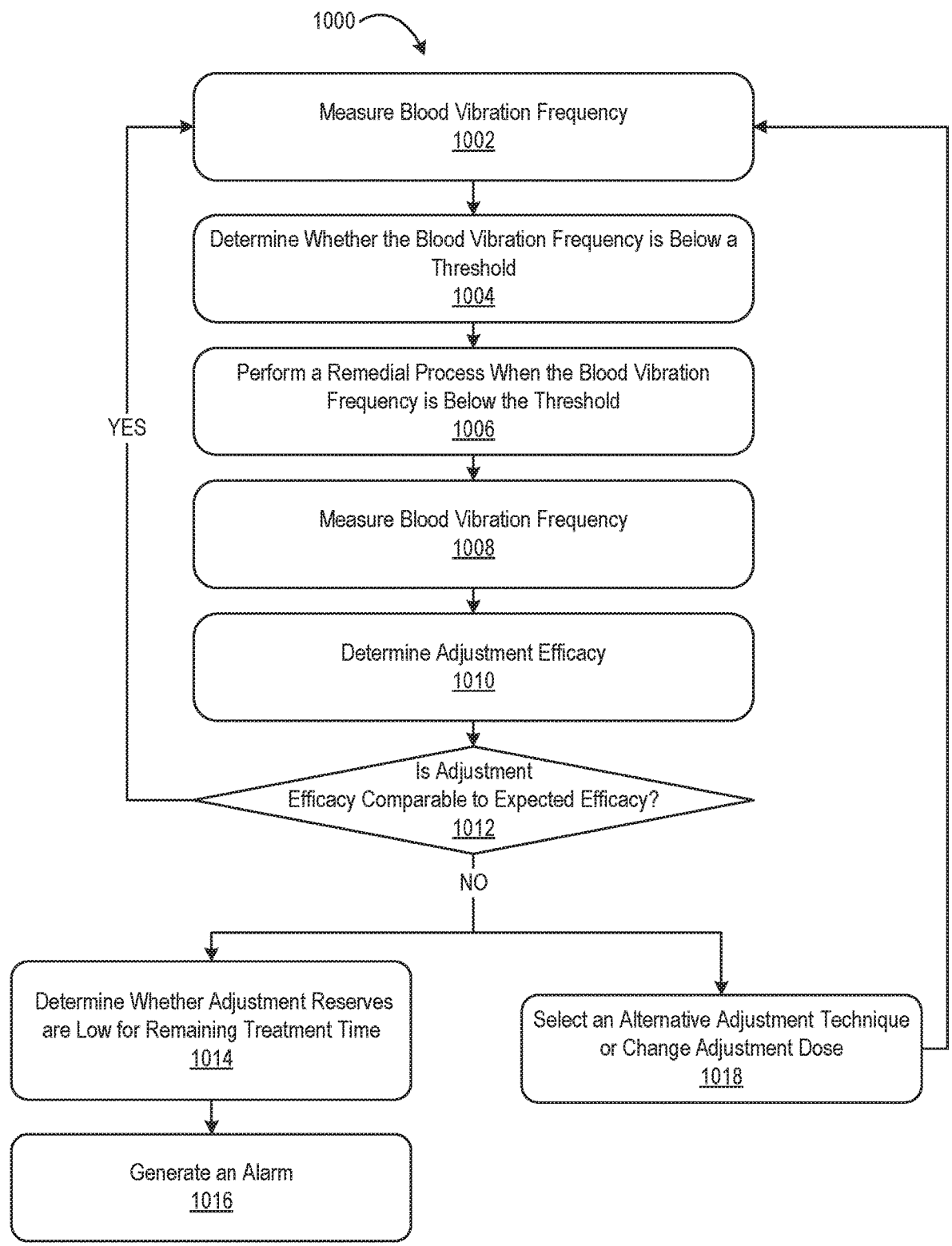
FIG. 10 is a flow diagram illustrating a process for monitoring clot neutralization efficacy according to some embodiments of the disclosure.

FIG. 10 is a flow diagram illustrating a process 1000 for monitoring clot neutralization efficacy according to some embodiments of the disclosure. At step 1002, the hemodialysis machine 12 uses the fiber-optic sensor to measure blood vibration frequency. At step 1004, the hemodialysis machine 12 determines whether the blood vibration frequency is below a threshold. At step 1006, the hemodialysis machine 12 performs a remedial process, wherein the remedial process includes making adjustments to the operation of the hemodialysis machine 12, when the blood vibration frequency is below the threshold, according to embodiments of the disclosure.

At step 1008, the hemodialysis machine 12 measures blood vibration frequency, and at step 1010, the hemodialysis machine 12 determines adjustment efficacy based on the adjustment made at step 1006. For example, the hemodialysis machine 12 can determine heparin infusion efficacy as previously discussed. In an embodiment, a similar procedure for determining heparin infusion efficacy is used to determine saline infusion efficacy.

At step 1012, the hemodialysis machine 12 determines whether the adjustment efficacy at step 1010 is comparable to an expected efficacy. For example, if the adjustment was heparin infusion, the expected efficacy can be a calibrated measure of an expected reaction of a patient's blood to a measured dose of heparin.

In some embodiments, the expected efficacy is a minimum reaction expected irrespective of the adjustment technique, i.e., any adjustment made at step 1006 should register at least the minimum reaction. At 1012, the hemodialysis machine 12 can determine whether the adjustment efficacy is greater than or equal to the expected efficacy. The expected efficacy is measured as a percentage increase in blood vibration frequency.

If the adjustment is comparable to the expected efficacy, then at step 1002, the hemodialysis machine 12 measures blood vibration frequency at step 1002. If the adjustment is not comparable to the expected efficacy, then the hemodialysis machine 12 can perform at least one of steps 1014 and 1018.

At step 1014, the hemodialysis machine 12 determines whether adjustment reserves are low for remaining treatment time. For example, the hemodialysis machine 12 can determine whether there is enough saline and/or heparin reserves to complete the dialysis treatment based on the remaining treatment time. If the adjustment reserves will not be enough to complete the hemodialysis treatment, at step 1016, the hemodialysis machine 12 can generate an alarm alerting the clinician of the low reserves.

If the adjustment efficacy is not comparable to expected efficacy or is not greater than a minimum efficacy at step 1012, then at step 1018, the hemodialysis machine 12 selects an alternative adjustment technique or changes adjustment dosage. For example, the hemodialysis machine 12 may switch from using the ultrasonic head to saline, or may switch from saline to heparin, and so on. The hemodialysis machine 12 may have stored dosages of saline and heparin, and may have stored settings for activating the ultrasonic head in either a constant low frequency mode or a higher frequency burst mode. The hemodialysis machine 12 may automatically change settings of a specific adjustment or select an alternative adjustment.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for monitoring blood clotting, comprising:
    circulating, by a dialysis system, blood through an extracorporeal circuit, wherein the blood flows from a patient to an input tubing of the extracorporeal circuit then to a dialyzer of the dialysis system and then back to the patient via an output tubing of the extracorporeal circuit;
    measuring, by a fiber-optic sensor of the dialysis system, blood vibration frequency of the blood flowing through the extracorporeal circuit;
    determining, by the dialysis system, whether the blood vibration frequency is below a threshold; and
    performing, by the dialysis system, a remedial process to address blood clotting in response to the blood vibration frequency being below the threshold.

2. The method according to claim 1, wherein performing the remedial process comprises:
    generating an alarm to alert a clinician, the alarm comprising a visual and/or auditory signal.

3. The method according to claim 1, wherein performing the remedial process comprises:
    dispensing saline in the extracorporeal circuit, the saline being dispensed via a saline tubing.

4. The method according to claim 1, wherein performing the remedial process comprises:
    dispensing heparin in the extracorporeal circuit, the heparin being dispensed via a heparin tubing.

5. The method according to claim 4, further comprising:
    measuring a second blood vibration frequency of the blood flowing through the extracorporeal circuit via a second fiber-optic sensor of the dialyzer system, wherein the second fiber-optic sensor is located downstream of the heparin tubing and the fiber-optic sensor is located upstream of the heparin tubing; and
    determining a heparin efficacy using the blood vibration frequency and the second blood vibration frequency.

6. The method according to claim 4, wherein the heparin tubing is located upstream of the fiber-optic sensor.

7. The method according to claim 1, wherein performing the remedial process comprises:
    emitting sound waves via an ultrasonic head of the dialysis system.

8. The method according to claim 7, wherein frequency of the sound waves are above 50 MHz and the sound waves are emitted in bursts.

9. The method according to claim 1, wherein performing the remedial process comprises:
    determining, based on a treatment time, that dialysis treatment is close to completion; and
    dispensing a volume of saline in the extracorporeal circuit, wherein the saline is dispensed via a saline tubing.

10. The method according to claim 1, further comprising:
    determining whether the blood vibration frequency is above an upper threshold limit based on an upper blood temperature limit; and
    generating an alarm in response to the blood vibration frequency being above the upper threshold limit.

11. A dialysis system for monitoring blood clotting comprising:
    a pump for pumping blood from a patient through an extracorporeal circuit;
    a dialyzer connected to the extracorporeal circuit;
    a fiber-optic sensor interfacing with the extracorporeal circuit, wherein the fiber-optic sensor is configured to measure blood vibration frequency at a location along the extracorporeal circuit; and
    a controller configured to: determine whether the blood vibration frequency is below a threshold, and perform a remedial process to address blood clotting in response to the blood vibration frequency being below the threshold.

12. The system according to claim 11, wherein performing the remedial process comprises:

generating an alarm to alert a clinician, the alarm comprising a visual and/or auditory signal.

13. The system according to claim 11, wherein performing the remedial process comprises:
providing a signal for dispensing saline in the extracorporeal circuit via a saline tubing connected to the extracorporeal circuit.

14. The system according to claim 11, wherein performing the remedial process comprises:
providing a signal for dispensing heparin in the extracorporeal circuit via a heparin tubing connected to the extracorporeal circuit.

15. The system according to claim 14, further comprising:
a second fiber-optic sensor interfacing with the extracorporeal tubing downstream of the heparin tubing, wherein the second fiber-optic sensor is configured to measure a second blood vibration frequency of the blood flowing through the extracorporeal circuit;
wherein the fiber-optic sensor is disposed upstream of the heparin tubing;
wherein the controller is further configured to determine a heparin efficacy using the blood vibration frequency of the fiber-optic sensor and the second blood vibration frequency of the second fiber-optic sensor.

16. The system according to claim 14, wherein the heparin tubing interfaces with the extracorporeal circuit at a location upstream of where the fiber-optic sensor interfaces with the extracorporeal circuit.

17. The system according to claim 11, further comprising:
an ultrasonic head interfacing with the extracorporeal tubing downstream from a location where the fiber-optic sensor interfaces with the extracorporeal tubing, the ultrasonic head being configured to emit sound waves for agitating the blood flowing through the extracorpreal circuit.

18. The system according to claim 17, wherein frequency of the sound waves are above 50 MHz and the sound waves are emitted in bursts.

19. A non-transitory computer readable medium having computer executable instructions stored thereon for monitoring blood clotting in a dialysis system, wherein the computer executable instructions, when executed, facilitate:
circulating blood through an extracorporeal circuit;
measuring blood vibration frequency of the blood flowing through the extracorporeal circuit;
determining whether the blood vibration frequency is below a threshold; and
performing a remedial process to address blood clotting in response to the blood vibration frequency being below the threshold.

20. The non-transitory computer readable medium according to claim 19, wherein performing the remedial process comprises:
generating an alarm to alert a clinician, the alarm comprising a visual and/or auditory signal.

* * * * *